(12) United States Patent
Ishida et al.

(10) Patent No.: US 9,175,946 B2
(45) Date of Patent: Nov. 3, 2015

(54) MEASURING METHOD OF HOLE DIAMETER, HOLE POSITION, HOLE SURFACE ROUGHNESS, OR BENDING LOSS OF HOLEY OPTICAL FIBER, MANUFACTURING METHOD OF HOLEY OPTICAL FIBER, AND TEST METHOD OF OPTICAL LINE OF HOLEY OPTICAL FIBER

(75) Inventors: Itaru Ishida, Sakura (JP); Shoji Tanigawa, Sakura (JP); Shoichiro Matsuo, Sakura (JP); Toshio Kurashima, Tsukuba (JP); Kazuhide Nakajima, Tsukuba (JP); Tomoya Shimizu, Tsukuba (JP); Takashi Matsui, Tsukuba (JP); Yukihiro Goto, Tsukuba (JP)

(73) Assignees: NIPPON TELEGRAPH AND TELEPHONE CORPORATION, Tokyo (JP); FUJIKURA LTD., Tokyo (JP)

( * ) Notice: Subject to any disclaimer, the term of this patent is extended or adjusted under 35 U.S.C. 154(b) by 655 days.

(21) Appl. No.: 13/213,328

(22) Filed: Aug. 19, 2011

(65) Prior Publication Data
US 2012/0044482 A1 Feb. 23, 2012

(30) Foreign Application Priority Data

Aug. 20, 2010 (JP) ................................. 2010-185319
Feb. 3, 2011 (JP) ................................. 2011-021886

(51) Int. Cl.
*G01N 21/00* (2006.01)
*H04B 17/00* (2015.01)
(Continued)

(52) U.S. Cl.
CPC ................ *G01B 11/08* (2013.01); *G01B 11/24* (2013.01); *G01B 11/30* (2013.01); *G01B 11/303* (2013.01); *G01B 11/306* (2013.01); *G01N 21/954* (2013.01); *G01N 21/958* (2013.01)

(58) Field of Classification Search
CPC ... G01N 21/958; G01N 21/954; G01B 11/08; G01B 11/12; G01B 11/16; G01B 11/24; G01B 11/2408; G01B 11/30; G01B 11/303; G01B 11/306; G01B 11/002; G01B 11/088; G01M 11/30; G01M 11/31; G01M 11/3109; G01M 11/3172; G01M 11/3118; G01M 11/3127; G01M 11/3136; G01M 11/3145; G01M 11/3154; G01M 11/3163; G01M 11/3181; G01M 11/319; G02B 6/02304
USPC ............................................. 356/73.1; 398/28
See application file for complete search history.

(56) References Cited

U.S. PATENT DOCUMENTS 4,838,690 A * 6/1989 Buckland et al. ............. 356/73.1
(Continued)

FOREIGN PATENT DOCUMENTS

EP        1 617 243 A1    1/2006
JP     2001-021735 A     1/2001
(Continued)

OTHER PUBLICATIONS

Tomoya Shimizu, et al., "A Study on Cutoff Wavelength Characteristics in Hole-Assisted Fiber", IEICE General Conference B13-24, Mar. 17, 2009, p. 512.
(Continued)

*Primary Examiner* — Tarifur Chowdhury
*Assistant Examiner* — Sunghee Y Gray
(74) *Attorney, Agent, or Firm* — Sughrue Mion, PLLC

(57) ABSTRACT

A measuring method of a hole diameter of a holey optical fiber includes calculating an arithmetical mean value I(x) from two backscattering light intensities at a position x of two backscattering light waveforms of the holey optical fiber, in which the two backscattering light waveforms are obtained by OTDR measurement; and obtaining the hole diameter at the position x, based on a correlation between an arithmetical mean value I(x) and an hole diameter of the holey optical fiber that is obtained in advance.

16 Claims, 8 Drawing Sheets

(51) Int. Cl.
*G01B 11/08* (2006.01)
*G01N 21/958* (2006.01)
*G01N 21/954* (2006.01)
*G01B 11/24* (2006.01)
*G01B 11/30* (2006.01)

(56) References Cited

U.S. PATENT DOCUMENTS

| | | | |
|---|---|---|---|
| 2002/0164139 A1* | 11/2002 | Saitou et al. | 385/127 |
| 2006/0285850 A1* | 12/2006 | Colpitts et al. | 398/108 |
| 2007/0283722 A1* | 12/2007 | Pathak et al. | 65/500 |
| 2009/0219516 A1* | 9/2009 | Bookbinder et al. | 356/73.1 |
| 2010/0014071 A1* | 1/2010 | Hartog | 356/73.1 |
| 2011/0276166 A1* | 11/2011 | Atanasoff | 700/104 |

FOREIGN PATENT DOCUMENTS

| | | | | |
|---|---|---|---|---|
| JP | 2002-145634 | A | | 5/2002 |
| JP | 2002-279575 | A | | 9/2002 |
| JP | 2003-004973 | A | | 1/2003 |
| JP | 3854627 | B2 | | 12/2006 |
| JP | 2007-298335 | A | | 11/2007 |
| JP | 4084762 | B2 | | 4/2008 |
| JP | 2010-003896 | A | | 1/2010 |
| WO | WO 8900675 | | * | 1/1989 ............ G01B 11/26 |

OTHER PUBLICATIONS

Masaharu Ohashi, "Novel OTDR Technique for Measuring Relative-Index Differences of Fiber Links", IEEE Photonics Technology Letters, Dec. 15, 2006, pp. 2584-2586, vol. 18, No. 24.

Jun-Ichi Yamamoto, et al., "Measurement technique of the fiber parameter distributions by using unidirectional OTDR", IEICE Technical Report OCS2005-89, 2006, pp. 1-6.

Kazuhide Nakajima, et al, "Single-Mode Hole-Assisted Fiber with Low Bending Loss Characteristics", Proceedings of the 58th IWCS/IICIT, 2009, pp. 264-269.

Alberto Rossaro, et al., "Spatially Resolved Chromatic Dispersion Measurement by a Bidirectional OTDR Technique", IEEE Journal on Selected Topics in Quantum Electronics, May/Jun. 2001, pp. 475-483, vol. 7, No. 3.

Notice of Allowance issued by Japanese Patent Office in Japanese Patent Application No. 2011-021886 dated Jun. 4, 2013.

Zhaoyang Wang, Evaluation of Optical Properties along Hole-Assisted Fibers by Using Bi-Directional OTDR Measurement, Proceedings of the 2010 IEICE Communications Society Conference, Japan, IEICE, Aug. 31, 2010, p. 317.

* cited by examiner

MEASURING METHOD OF HOLE DIAMETER, HOLE POSITION, HOLE SURFACE ROUGHNESS, OR BENDING LOSS OF HOLEY OPTICAL FIBER, MANUFACTURING METHOD OF HOLEY OPTICAL FIBER, AND TEST METHOD OF OPTICAL LINE OF HOLEY OPTICAL FIBER

BACKGROUND OF THE INVENTION

1. Field of the Invention

The present invention relates to a method of non-destructively measuring a hole diameter, a hole position, a hole surface roughness, or a bending loss of a holey optical fiber, a manufacturing method of a holey optical fiber employing the measuring method, and a test method of an installed optical line having a holey optical fiber.

Priorities are claimed on Japanese Patent Application No. 2010-185319, filed Aug. 20, 2010, and Japanese Patent Application No. 2011-021886, filed Feb. 3, 2011, the contents of which are incorporated herein by reference.

2. Description of Related Art

A holey optical fiber has a structure in which a plurality of holes is formed in an optical fiber made of quartz glass or the like, and these holes are extended along the longitudinal direction of the optical fiber. The holey optical fiber can obtain optical properties that cannot be realized in conventional optical fibers due to the presence of the holes.

For example, as reported in Japanese Patent No. 3854627 and K. Nakajima et al., 58th IWCS, 9-3, 2009, in a hole assist optical fiber in which a plurality of holes is arranged around a core with a high refractive index, marked improvements of bending loss characteristics are expected due to the increase of an effective refractive index difference by the holes.

Such a holey optical fiber is obtained by drawing a holey optical fiber preform, for example, as described in Japanese Unexamined Patent Application, First Publication No. 2002-145634 or the like. Additionally, the holey optical fiber preform is obtained by a hole opening method, such as a drilling method of performing drilling work on an optical fiber preform, thereby a hole opening is preformed.

The drawing of a holey optical fiber is performed by a method of injecting gas, such as nitrogen gas, into holes of a preform and pressurizing the gas, and a holey optical fiber with a desired hole diameter is obtained by controlling the pressure of the gas to be injected.

On the other hand, it is known that the hole diameter of the holey optical fiber influences the optical properties greatly. For example, it is known that, the smaller the hole diameter of the hole assist optical fiber, the weaker the light confinement effect, whereby the bending loss increases. As such, since the hole diameter is a factor that influences optical properties, it is necessary to maintain the hole diameter of the holey optical fiber at a constant value in the longitudinal direction.

As mentioned above, since the hole diameter of the holey optical fiber influences the optical properties greatly, it is necessary to evaluate the uniformity of the hole diameter in the longitudinal direction. Specifically, it is necessary to guarantee the quality by cutting the holey optical fibers along the longitudinal direction and measuring the hole diameter at the cutting end face and the optical properties.

In this method, since the length of the holey optical fiber is short, manufacture of a long optical cable is difficult, and additionally, this method is insufficient as a quality guarantee method of the optical properties in the longitudinal direction. In order to avoid such a problem, method for non-destructively measuring the hole diameter of the holey optical fiber in the longitudinal direction, and guaranteeing optical properties, such as bending loss, is needed.

As a solution, a method of measuring the hole diameter during a drawing process is proposed in Japanese Patent No. 4084762. This method makes light enter an optical fiber from one end thereof during the drawing process to perform OTDR measurement, and measures the attenuation amount of backscattering light caused by bending the optical fiber, thereby the internal diameter of the hole is estimated.

However, in this method, it is necessary to bend the holey optical fiber with a bending diameter of 10 to 20 mm during the drawing process. Therefore, the holey optical fiber may be locally broke due to a bending stress, and a problem such as a poor productivity occurs. Additionally, in case of a holey optical fiber which has a small bending loss like the hole assist optical fiber, measurement of the attenuation amount of the backscattering light becomes difficult.

Additionally, it is also necessary to know the values in the longitudinal direction of the hole position and hole surface roughness that affect the characteristics of the holey optical fiber.

SUMMARY

An object of an aspect of the invention is to simply estimate the hole diameter of a holey optical fiber and estimate the bending loss without cutting the holey optical fiber while measuring the hole diameter of the holey optical fiber.

An object of the other aspect of the invention is to estimate the hole position and hole surface roughness that affect the characteristics of the holey optical fiber, without cutting this optical fiber.

Additionally, an object of the other aspect of the invention is to obtain a method of manufacturing a holey optical fiber that can guarantee the bending loss value by employing this measuring method to control a bending loss value, and to obtain a test method of an optical line having holey optical fibers to which this measuring method is employed.

In order to solve these problems, a first aspect of the invention relates to a measuring method of a hole diameter of a holey optical fiber. The measuring method of a hole diameter of a holey optical fiber includes calculating an arithmetical mean value $I(x)$ from two backscattering light intensities at a position x of two backscattering light waveforms of the holey optical fiber, in which the two backscattering light waveforms is obtained by OTDR measurement, and obtaining the hole diameter at the position x, based on a correlation between an arithmetical mean value $I(x)$ and a hole diameter of the holey optical fiber that is obtained in advance.

A second aspect of the invention relates to a measuring method of a bending loss of a holey optical fiber. The measuring method of a bending loss of a holey optical fiber includes calculating an arithmetical mean value $I(x)$ from two backscattering light intensities at a position x of two backscattering light waveforms of the holey optical fiber, in which the two backscattering light waveforms is obtained by OTDR measurement, and obtaining the bending loss at the position x, based on a correlation between an arithmetical mean value $I(x)$ and a bending loss of the holey optical fiber that is obtained in advance.

A third aspect of the invention relates to a measuring method of a hole position of a holey optical fiber. The measuring method of a hole position of a holey optical fiber includes calculating an arithmetical mean value $I(x)$ from two backscattering light intensities at a position x of two backscattering light waveforms of the holey optical fiber, in which the two backscattering light waveforms is obtained by OTDR measurement, and obtaining the hole position at the position x, based on a correlation between an arithmetical mean value I(x) and a hole position of the holey optical fiber that is obtained in advance.

A fourth aspect of the invention relates to a measuring method of a hole surface roughness of a holey optical fiber. The measuring method of a hole surface roughness of a holey optical fiber includes calculating an arithmetical mean value I(x) from two backscattering light intensities at a position x of two backscattering light waveforms of the holey optical fiber, in which the two backscattering light waveforms is obtained by OTDR measurement, and obtaining the surface roughness of the holes at the position x, based on a correlation between an arithmetical mean value I(x) and an surface roughness of the holes of the holey optical fiber that is obtained in advance.

A fifth aspect of the invention relates to a measuring method of a hole diameter of a holey optical fiber. The measuring method of a hole diameter of a holey optical fiber includes calculating an arithmetical mean value $I_{ref}$ at an optical fiber portion for reference and an arithmetical mean value $I_{hf}(x)$ at a position x of the holey optical fiber, from two backscattering light waveforms, obtained by OTDR measurement, of a connected optical fiber formed by connecting optical fibers for reference to both ends of the holey optical fiber respectively; obtaining a difference ΔI between the arithmetical mean value $I_{hf}(x)$ and the arithmetical mean value $I_{ref}$; and obtaining the hole diameter at the position x, based on a correlation between a difference ΔI and a hole diameter of the holey optical fiber that is obtained in advance.

A sixth aspect of the invention relates to a measuring method of a bending loss of a holey optical fiber. The measuring method of a bending loss of a holey optical fiber includes calculating an arithmetical mean value $I_{ref}$ at an optical fiber portion for reference and an arithmetical mean value $I_{hf}(x)$ at a position x of the holey optical fiber, from two backscattering light waveforms, obtained by OTDR measurement, of a connected optical fiber formed by connecting optical fibers for reference to both ends of the holey optical fiber respectively; obtaining a difference ΔI between the arithmetical mean value $I_{hf}(x)$ and the arithmetical mean value $I_{ref}$; and obtaining the bending loss at the position x, based on a correlation between a difference ΔI and a bending loss of the holey optical fiber that is obtained in advance.

A seventh aspect of the invention relates to a measuring method of a hole position of a holey optical fiber. The measuring method of a hole position of a holey optical fiber includes calculating an arithmetical mean value $I_{ref}$ at an optical fiber portion for reference and an arithmetical mean value $I_{hf}(x)$ at a position x of the holey optical fiber, from two backscattering light waveforms, obtained by OTDR measurement, of a connected optical fiber formed by connecting optical fibers for reference to both ends of the holey optical fiber respectively; obtaining a difference ΔI between the arithmetical mean value $I_{hf}(x)$ and the arithmetical mean value $I_{ref}$; and obtaining the hole position at the position x, based on a correlation between a difference ΔI and a hole position of the holey optical fiber that is obtained in advance.

An eighth aspect of the invention relates to a measuring method of a hole surface roughness of a holey optical fiber. The measuring method of a hole surface roughness of a holey optical fiber includes calculating an arithmetical mean value $I_{ref}$ at an optical fiber portion for reference and an arithmetical mean value $I_{hf}(x)$ at a position x of the holey optical fiber, from two backscattering light waveforms, obtained by OTDR measurement, of a connected optical fiber formed by connecting optical fibers for reference to both ends of the holey optical fiber respectively; obtaining a difference ΔI between the arithmetical mean value $I_{hf}(x)$ and the arithmetical mean value $I_{ref}$; and obtaining the hole surface roughness at the position x, based on a correlation between a difference ΔI and a hole surface roughness of the holey optical fiber that is obtained in advance.

The optical fiber for reference may be a single mode optical fiber.

A ninth aspect of the invention relates to a measuring method of a hole diameter of a holey optical fiber. The measuring method of a hole diameter of a holey optical fiber includes deriving a mode field diameter 2W(x) using an arithmetical mean value I(x) calculated from two backscattering light intensities at a position x of two backscattering light waveforms, obtained by OTDR measurement, of the holey optical fiber, and obtaining the hole diameter at the position x, based on a correlation between a mode field diameter 2W(x) and a hole diameter of the holey optical fiber that is obtained in advance.

A tenth aspect of the invention relates to a measuring method of a bending loss of a holey optical fiber. The measuring method of a bending loss of a holey optical fiber includes deriving a mode field diameter 2W(x) using an arithmetical mean value I(x) calculated from two backscattering light intensities at a position x of two backscattering light waveforms, obtained by OTDR measurement, of the holey optical fiber, and obtaining the bending loss value at the position x, based on a correlation between a mode field diameter 2W(x) and a bending loss value of the holey optical fiber that is obtained in advance.

An eleventh aspect of the invention relates to a test method of an optical line which includes detecting a bending loss and a defect portion of the bending loss of an installed optical line having a holey optical fiber using the measuring method of a bending loss.

A twelfth aspect of the invention relates to a manufacturing method of a holey optical fiber. The manufacturing method of a holey optical fiber includes manufacturing a holey optical fiber by melting and drawing an optical fiber preform formed with holes; measuring a hole diameter, a hole position, a hole surface roughness, or a bending loss of the holey optical fiber using the measuring method.

In the measuring method according to the aspect of the invention, it is proved that a high correlation is present between the arithmetical mean value and a hole diameter, a hole position, or a hole surface roughness of the holey optical fiber, in which the arithmetical mean value is obtained from the backscattering light intensities obtained by performing the OTDR measurement on the holey optical fiber For this reason, according to the measuring method of the aspect of the invention, the arithmetical mean value is calculated from the backscattering light intensities at a position of the two backscattering light waveforms obtained by the OTDR measurement, and the hole diameter, the hole position, and the hole surface roughness at the position can be obtained based on the correlation between the arithmetical mean value and the hole diameter, the hole position, and the hole surface roughness that is obtained in advance.

Accordingly, the bending loss with a high correlation with the hole diameter can be estimated from the obtained hole diameter without needing to cut the holey optical fiber.

Additionally, according to the test method of an optical line of the aspect of the invention, the bending loss value at an arbitrary point in an installed optical line having holey optical fibers can be known, and a defect portion where the bending loss increases can be identified. Therefore, a position where an excessive external force is applied during the installation of an optical line or the like and the bending loss is increased can be detected. This contributes to the operation of the optical line.

Additionally, according to the manufacturing method of the aspect of the invention, the bending loss value of the holey optical fiber obtained by melting and drawing can be estimated. As a result, it is possible to guarantee the quality of a holey optical fiber, and a holey optical fiber whose quality is guaranteed over the entire length of the holey optical fiber can be provided. Additionally according to this manufacturing method, a holey optical fiber that keeps the bending loss value within prescribed values or lower can be manufactured. Additionally, the hole position and hole surface roughness of a holey optical fiber can be estimated, and a holey optical fiber that keeps these values within prescribed values can be manufactured.

DETAILED DESCRIPTION OF THE PREFERRED EMBODIMENTS

A measuring method or a test method according to an embodiment of the invention employs the bidirectional OTDR measurement technique to estimate the hole diameter, the hole position, the hole surface roughness, or the bending loss in the longitudinal direction of a holey optical fiber.

The bidirectional OTDR measurement technique in the invention is defined as including a total reflection OTDR measurement technique.

The bidirectional OTDR measurement technique is, as shown in ITU-T G. 650. 1, a measurement technique capable of acquiring backscattering light waveforms from both directions of an optical fiber by the OTDR, and acquiring structural changes in core diameter, relative index difference, or the like in the longitudinal direction from the waveforms.

The total reflection OTDR measurement technique connects a total reflection terminator to one end (far end; a first end) of an optical fiber, makes measurement light enter from the other end (near end; a second end), and obtains backscattering light waveforms substantially from both directions. Also, the total reflection OTDR measurement technique is capable of acquiring structural changes in core diameter, relative index difference, or the like in the longitudinal direction from the waveforms. The total reflection OTDR measurement technique has the same function as the bidirectional OTDR measurement technique.

For such a reason, the total reflection OTDR measurement technique is included in the bidirectional OTDR measurement technique.

For this reason, the following embodiments are described with an original bidirectional OTDR measurement technique and the total reflection OTDR measurement technique being distinguished from each other.

First, a method of obtaining the hole diameter and bending loss of a holey optical fiber will be described.

As a result of repeating various kinds of study, when the bidirectional OTDR measurement was performed on the holey optical fiber, it was proved that obtained backscattering light waveforms have a high correlation with the hole diameter.

Figure 1:
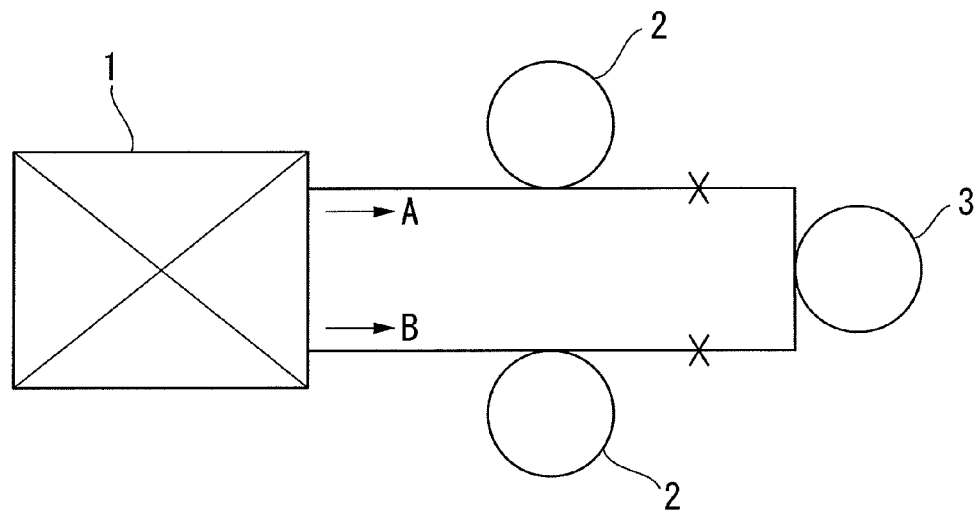
FIG. 1 is a schematic configuration view showing an embodiment of a measuring method of the invention.

FIG. 1 shows one embodiment of a measuring method of hole diameter or bending loss of the invention, and this embodiment is performed by the bidirectional OTDR measuring method.

Reference numeral 1 in the drawing designates a well-known bidirectional OTDR measuring equipment. Two optical fibers for reference 2, 2 are respectively connected to both ends of a holey optical fiber 3 having a length L. Both the ends of the holey optical fiber 3 are connected to the bidirectional OTDR measuring equipment 1, in which the optical fibers for reference 2, 2 are connected to both the ends of the holey optical fiber 3.

Thereby, measurement light is made to enter in each measurement direction, namely a direction A and a direction B, respectively, and both the backscattering light waveform $S_A$ and $S_B$ of the direction A and the direction B are obtained.

The optical fibers for reference 2, 2 may have either a holey optical fiber or hole-less optical fiber. A single mode optical fiber in which optical properties are known and the optical properties are stabilized in the length direction is desirable as the optical fibers for reference 2, 2. The lengths of two single mode optical fibers may be equal to each other or different from each other, and it is normally sufficient if the lengths are 2 to 5 km.

As for the two obtained backscattering light waveforms $S_A$ and $S_B$, if the arithmetical mean value of backscattering light intensity is calculated in spots whose positions in the holey optical fiber 3 coincide with each other, an arithmetical mean waveform is obtained. For example, when backscattering light intensity at a position with a length x from the direction A is defined as $S_A(x)$ and backscattering light intensity at a position with a length L−x from the direction B is defined as $S_B(L-x)$, the arithmetical mean value I(x) is expressed by the following Formula (1). The arithmetical mean value I(x) is a value at a certain position x of a connected optical fiber obtained by connecting the two optical fibers for reference 2, 2 to the holey optical fiber 3.

$$I(x) = \frac{S_A(x) + S_B(L-x)}{2} \quad (1)$$

Figure 2:
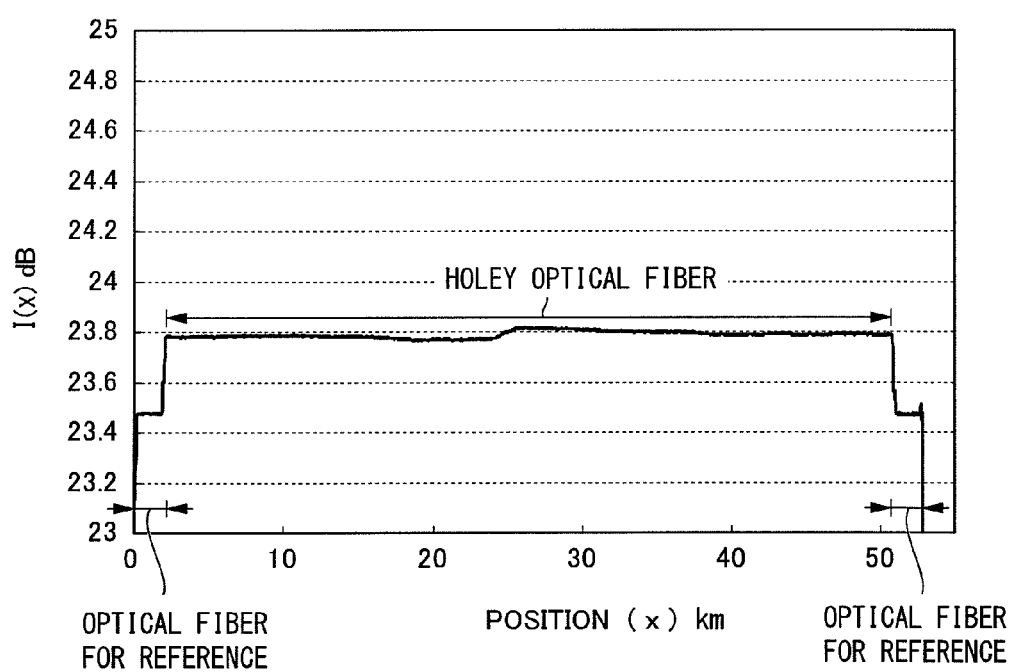
FIG. 2 is a graph showing a change in an arithmetical mean value I(x) in a longitudinal direction of a holey optical fiber in the embodiment.

FIG. 2 shows the result of a change in the optical fiber longitudinal direction of the arithmetical mean value I(x) calculated from the backscattering light waveform $S_A$ and the backscattering light waveform $S_B$ that are obtained by the bidirectional OTDR measurement when the hole-less single mode optical fibers with a length of about 2 km serving as the optical fibers for reference 2, 2 are connected to both sides of the holey optical fiber 3 with a length of about 50 km.

As a result of study, it was found that there is a correlation between the change in the arithmetical mean value I(x) obtained from the bidirectional OTDR measurement, and a change in the hole diameter actually obtained by cross-sectional measurement of the holey optical fiber, and the hole diameter can be approximated by a linear function of the arithmetical mean value I(x).

Additionally, in the case of the hole assist optical fiber that can reduce the bending loss greatly due to the presence of holes, it is known that the bending loss characteristics of the optical fiber vary depending on the diameter of the holes. This shows a possibility that the bending loss characteristics or cutoff wavelength characteristics in the longitudinal direction of the hole assist optical fiber can be estimated from the arithmetical mean value I(x) obtained from the bidirectional OTDR measurement. As a result of actually performing verification, it was found that there is a correlation between the arithmetical mean value I(x) and the bending loss, and the bending loss can be approximated as an exponential function of the arithmetical mean value.

Moreover, when holey optical fibers with different measurement lengths are compared, the absolute value of the arithmetical mean value I(x) varies depending on the measurement lengths. Therefore, a hole diameter fluctuation and an optical property fluctuation in the longitudinal direction of the holey optical fiber may be evaluated, according to the difference ΔI defined by the following formula. The influence of the measurement lengths can be eliminated by using the difference ΔI.

$$\Delta I = I_{hf} - I_{ref} \quad (2)$$

Figure 3:
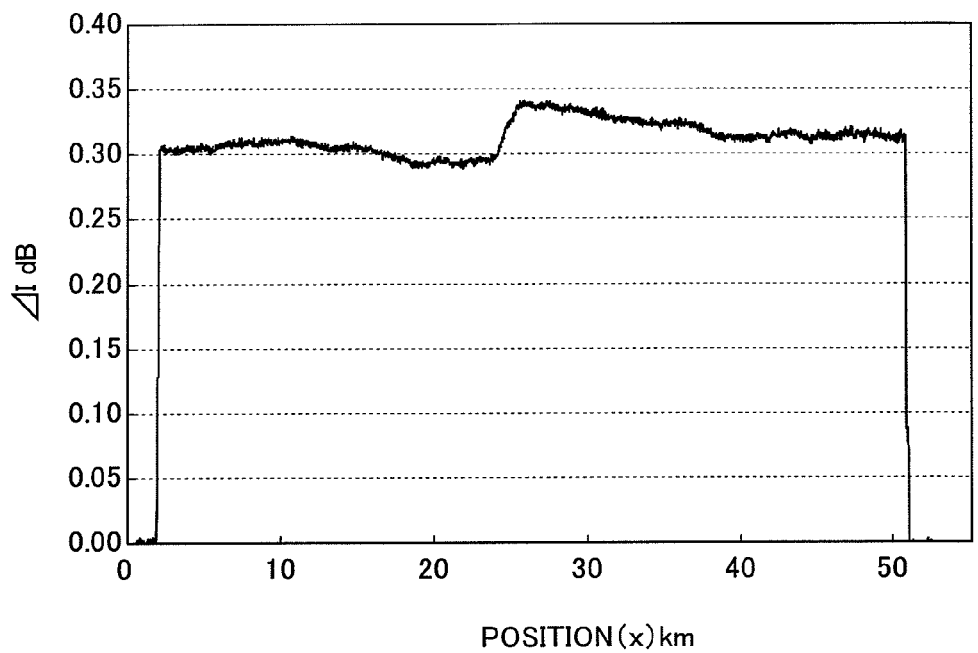
FIG. 3 is a graph showing a change in a difference ΔI in the longitudinal direction of the holey optical fiber in an embodiment.

$I_{hf}$: Arithmetical mean value I(x) of holey optical fiber
$I_{ref}$: Arithmetical mean value I(x) of optical fiber for reference FIG. 3 shows a result of which the change in the longitudinal direction of the arithmetical mean value I(x) of FIG. 2 is converted into a change in the longitudinal direction of the difference ΔI.

Additionally, the optical properties of terminals of the holey optical fiber that is an object to be measured may be measured in advance, and the difference ΔI may be estimated by a value normalized by the obtained optical property values of the terminals.

In practice, an optical fiber preform has slight manufacture variation in structural parameters, such as the core diameter and the relative index difference, between manufacture lots or in the longitudinal direction of the preform. Therefore, by using the normalized difference ΔI, the influence on the correlation caused by the manufacture variation between manufacture lots and the manufacture variation in the longitudinal direction of the preform can be reduced, and the hole diameter and bending loss in the longitudinal direction of the optical fiber can be estimated with a high accuracy.

A specific example of the normalized technique first measures the mode field diameter 2W and cutoff wavelength λc at the terminals of the holey optical fiber that is an object to be measured. Thereafter, the difference ΔI is obtained as mentioned above by the bidirectional OTDR measurement. The normalization includes conversion into ΔI/(2W/λc).

Additionally, in the measuring method of the hole diameter or bending loss according to an embodiment of the invention, the mode field diameter can be calculated from the arithmetical mean value I(x) of the holey optical fiber obtained from the bidirectional OTDR measurement, and the hole diameter and the bending loss value can be estimated from the mode field diameter.

As a calculation method of the mode field diameter 2W(x) from the arithmetical mean value I(x) at a point with a length x of the holey optical fiber, the mode field diameter can be obtained from the following Formula (3) described in ITU-T G. 650. 1.

$$2W(x) = 2W(x_0) \cdot 10^{(-(I(x) - I(x_0)) + k)/20)} \quad (3)$$

Here, $2W(x_0)$ is a mode field diameter at the point $x_0$, $I(x_0)$ is an arithmetical mean value at the point $x_0$, and k is a constant expressed by the following formula.

$$k = 10 \cdot \log\left[\left\{\frac{1 + 0.62\Delta(x)}{1 + 0.62\Delta(x_0)}\right\}\left\{\frac{50 - \Delta(x)}{50 - \Delta(x_0)}\right\}\right]$$

Accordingly, if a mode field diameter $2W(x_0)$ at the point $x_0$ is measured in advance, the mode field diameter 2W(x) at the point x can be calculated.

Additionally, as described in a literature, A. Rossaro et al., "Spatially resolved chromatic dispersion measurement by a bidirectional OTDR technique," IEEE J. Sel. Topics Quantum Electron., 7, 475-483 (2001), the mode field diameter 2W(x) can also be calculated from the arithmetical mean value I(x) using the following Formula (4).

$$2W(x) = 2W(x_0) \cdot [2W(x_1)/2W(x_0)]^{((I(x) - I(x_0))/(I(x_1) - I(x_0)))} \quad (4)$$

Here, $2W(x_1)$ is a mode field diameter at a point $x_1$, and $I(x_1)$ is an arithmetical mean value at the point $x_1$. This method first measures the mode field diameters $2W(x_0)$ and $2W(x_1)$ at the point $x_0$ and the point $x_1$ in advance, and then calculates the mode field diameter 2W(x) at the point x.

Here, the mode field diameters $2W(x_0)$ and $2W(x_1)$ at the point $x_0$ and the point $x_1$ and the arithmetical mean values $I(x_0)$ and $I(x_1)$ may be the values of the optical fibers for reference, and may be the values of terminal points of the holey optical fiber.

In the embodiment of the invention, it was found that there is a correlation between the mode field diameter, hole diameter, and bending loss of the holey optical fiber.

Hereinafter, specific examples will be shown and described in detail.

Figure 4:
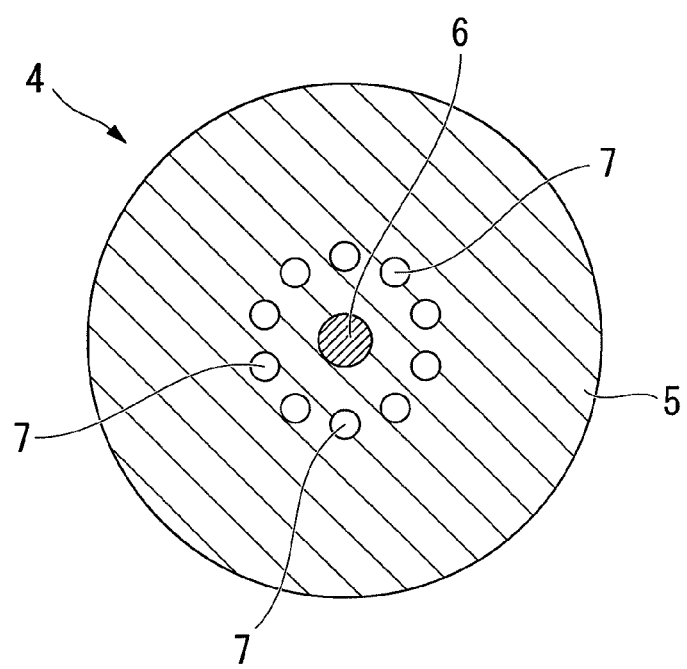
FIG. 4 is a schematic configuration view showing the cross-sectional structure of the holey optical fiber used in the embodiment.

FIG. 4 shows a holey optical fiber used for the present specific example. This holey optical fiber is a hole assist optical fiber 4 with an external diameter of 125 μm that is formed such that ten holes 7 are equally arranged on the same circumference in cladding 5 made of silica around the vicinity of a core 6 with a high refractive index made of germanium-doped silica.

Using the measurement system shown in FIG. 1, hole-less single mode optical fibers with a length of 2 km were connected as the optical fibers for reference 2, 2, and the arithmetical mean value I(x) is measured. In addition, the measurement wavelength was 1550 nm.

First, a hole assist optical fiber in which the hole diameter greatly fluctuates in the longitudinal direction of the optical fiber is prepared, and the change in the longitudinal direction of the difference ΔI obtained from the measurement of the arithmetical mean value I(x) and an actual hole diameter change are investigated. In the measuring method of the actual hole diameter, the hole assist optical fiber is cut, and measurement of the cut end face portion is performed using an optical microscope.

Figure 5:
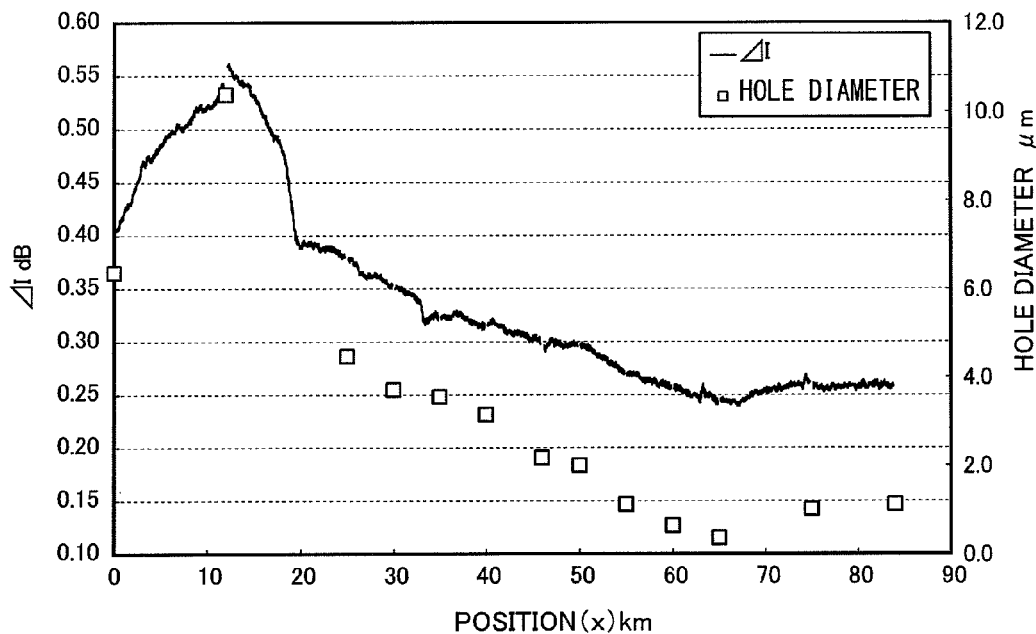
FIG. 5 is a graph showing the relation between the difference ΔI and the hole diameter in a hole assist optical fiber as a change in the longitudinal direction.

FIG. 5 shows the comparison between a fluctuation in the difference ΔI and a fluctuation in the hole diameter in the longitudinal direction of a hole assist optical fiber. It is apparent that the fluctuation in the hole diameter coincides with the fluctuation in the difference ΔI well.

From this, if the difference ΔI at the position (x) in the longitudinal direction of the hole assist optical fiber is calculated, the hole diameter at the position (x) can be known. It is known that there is a strong correlation between the hole diameter and the bending loss of the hole assist optical fiber. Thus, bending loss can also be known directly from the difference ΔI.

In fact, the hole diameter and bending loss of a plurality of hole assist optical fibers with different hole diameters are measured, and the comparison with the difference ΔI is performed. Measurement of the bending loss is obtained by a measuring method based on IEC60793-1-47, and the bending loss value is obtained when a bending radius is 5 mm and the measurement wavelength is 1550 nm.

Figure 6:
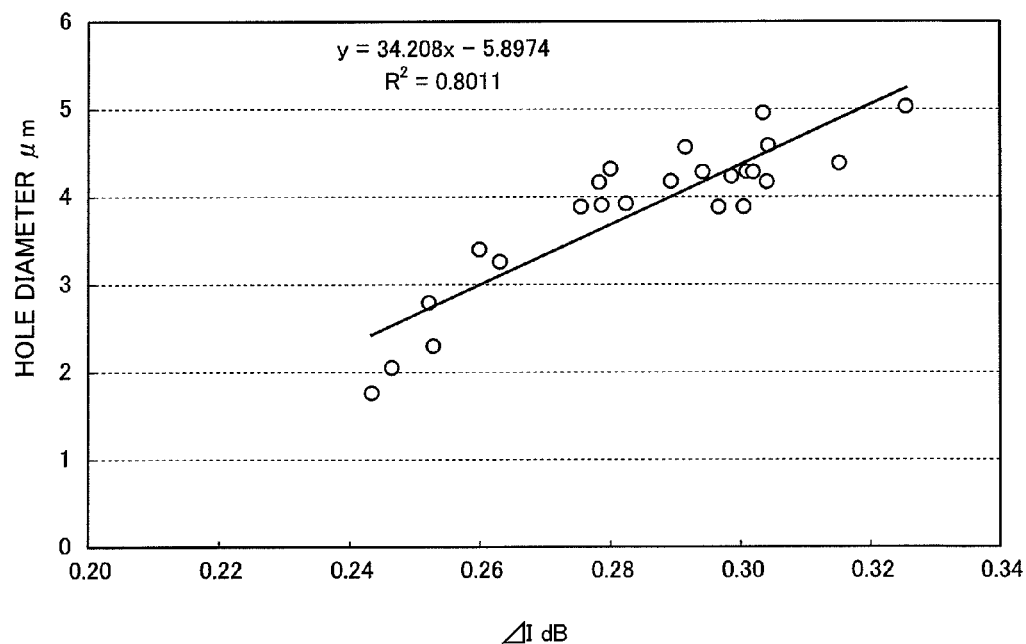
FIG. 6 is a graph showing the correlation between the hole diameter and the difference ΔI.
Figure 7:
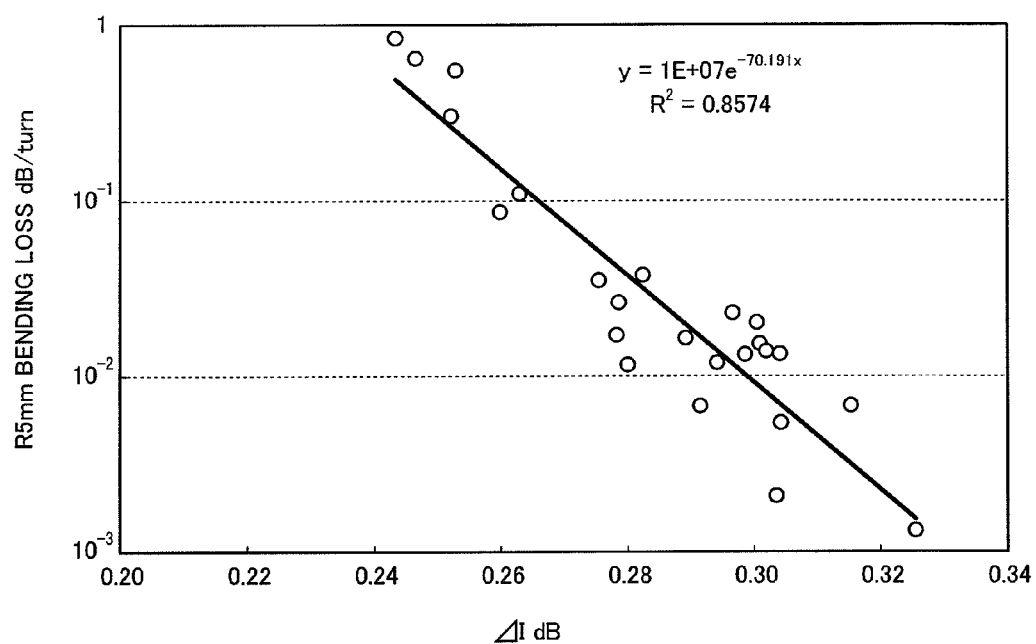
FIG. 7 is a graph showing the correlation between a bending loss value and the difference ΔI.

The relation between the difference ΔI and the hole diameter is shown in FIG. 6, and the relation between the difference ΔI and the bending loss is shown in FIG. 7. The difference ΔI and the hole diameter, or the difference ΔI and the bending loss showed an excellent correlation, and it is confirmed that the hole diameter can be approximated by a linear function of the difference ΔI.

Accordingly, if the relation between the difference ΔI and the position (x) in the longitudinal direction of the optical fiber as shown in FIG. 2 is obtained for one holey optical fiber, using the bidirectional OTDR measurement technique, the difference ΔI at an arbitrary position (x) can be obtained, and a fluctuation in the hole diameter or a fluctuation in the bending loss in the longitudinal direction of the holey optical fiber can be estimated from the correlation shown in FIG. 6 or FIG. 7 based on the difference ΔI.

In addition, although the example in which a connected fiber formed by connecting two optical fibers for reference to both ends of a holey optical fiber is used as an object to be measured is given in the aforementioned description, the connected fiber formed by connecting the optical fibers for reference is not necessarily used.

Measurement light is made to enter both ends of the holey optical fiber 3 directly from the bidirectional OTDR measuring equipment 1 so as to obtain two backscattering light waveforms, and the relation between the arithmetical mean value I(x) and the position (x) as shown in FIG. 2 is obtained. It is confirmed that a correlation similar to the correlation as shown in FIG. 6 or FIG. 7 is present between the arithmetical mean value I(x) and an actual hole diameter or between the arithmetical mean value I(x) and an actual bending loss. For this reason, the hole diameter fluctuation and optical property fluctuation in the longitudinal direction of the holey optical fiber can be similarly estimated.

However, as compared with a case where optical fibers for reference are connected and measured, the correlativity between the arithmetical mean value I(x) and the hole diameter becomes lower.

Generally, in the OTDR measuring method, when measurement light is made to enter a target optical fiber from the OTDR measuring equipment, it is known that the intensity of backscattering light that returns from a position up to several kilometers from an incident end is unsuitable for measurement and is inferior in measurement accuracy due to factors such as noise. Therefore, even in conventional OTDR measurement, a technique of connecting optical fibers for reference to an optical fiber serving as an object to be measured is adopted.

Even in the measuring method of the embodiment of the invention, high correlativity is obtained by connecting two optical fibers for reference for the same reason. However, even when the optical fibers for reference are not connected, sufficient correlativity is obtained if the arithmetical mean value I(x) at a position distant from the incident end is obtained, and the hole diameter can be estimated.

Next, a method of calculating the mode field diameter from the arithmetical mean value I(x) and estimating the hole diameter or the bending loss from this mode field diameter will be specifically described.

A fiber used for measurement is the hole assist optical fiber shown in FIG. 4, and the mode field diameters $2W(x_0)$ and $2W(x_1)$ at both terminals of the hole assist optical fiber are measured in advance using the measuring method based on ITU-T G. 650. 1. The measurement wavelength of the mode field diameter is 1550 nm. Moreover, the mode field diameter $2W(x)$ at the point x is calculated using Formula (4) from the arithmetical mean value I(x) obtained from the bidirectional OTDR measurement.

Figure 8:
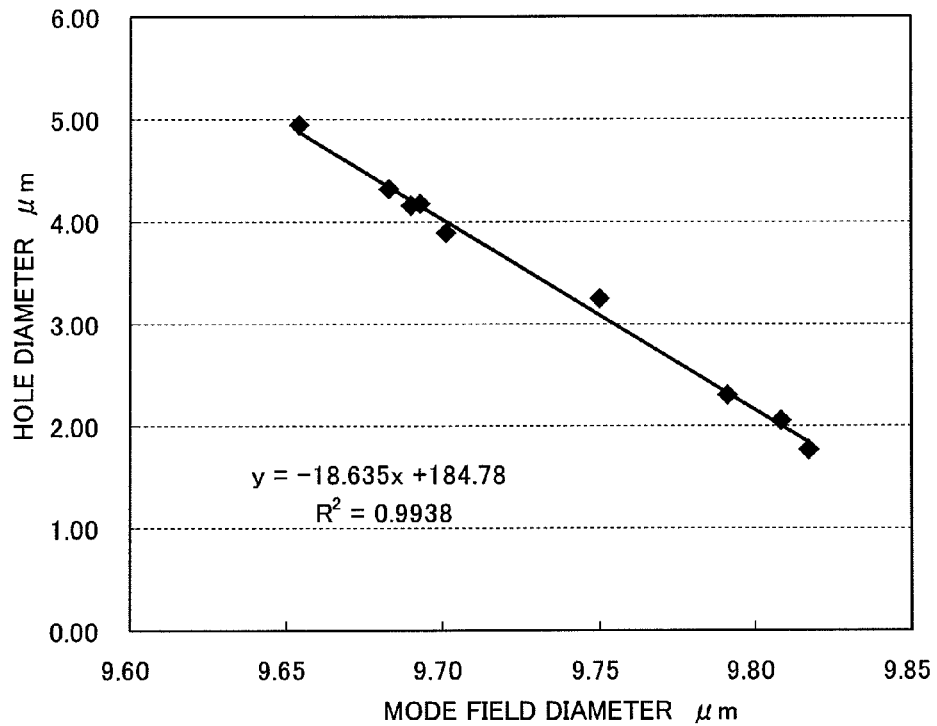
FIG. 8 is a graph showing the correlation between a mode field diameter and the hole diameter.

The relation between the calculated mode field diameter and an actually measured hole diameter is shown in FIG. 8. A correlation is recognized between the calculated mode field diameter 2W and the hole diameter d, and can be approximated by a linear function of the following Formula (5).

$$d \approx a_1 + a_2 \times 2W \qquad (5)$$

Figure 9:
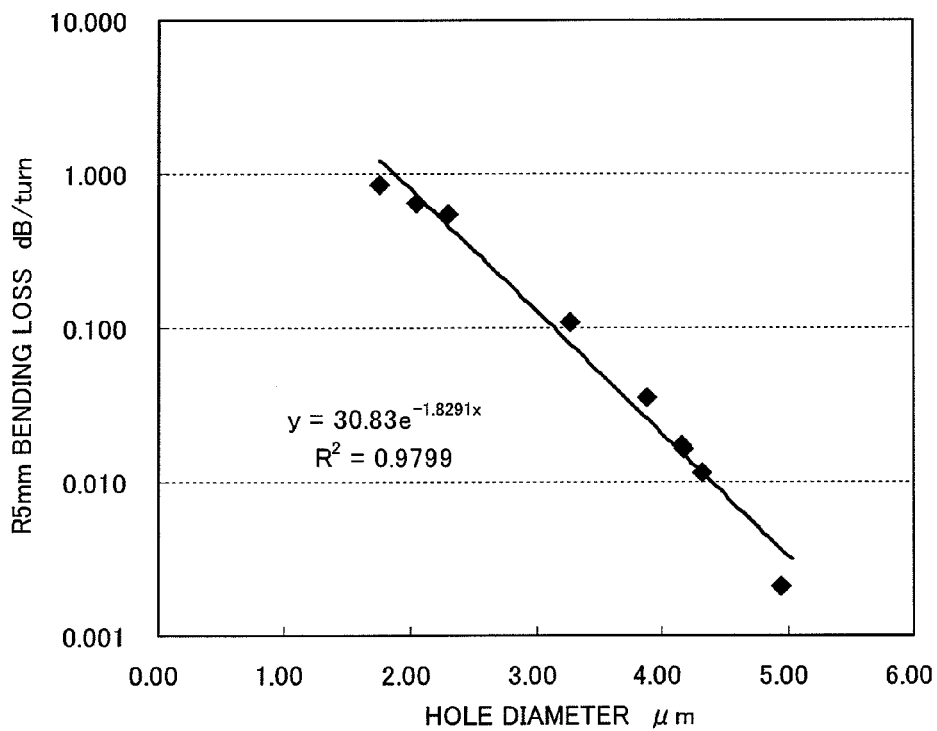
FIG. 9 is a graph showing the correlation between the hole diameter and the bending loss value.

Moreover, FIG. 9 shows the relation between the hole diameter and the bending loss value (bending radius of 5 mm and measurement wavelength of 1550 nm). It is apparent that the hole diameter and the bending loss value $\alpha_b$ can be approximated by an exponential function of the following formula (6).

$$\alpha_b \approx b_1 \times \exp(b_2 \times d) \qquad (6)$$

As described above, the distribution of the hole diameter or bending loss value in the longitudinal direction can be estimated by calculating the correlation between the calculated mode field diameter and the actually measured hole diameter or bending loss value in advance, and determining constants $a_1$, $a_2$, $b_1$, and $b_2$ of Formula (5) and Formula (6).

In addition, this estimation method can also be applied to a holey optical fiber having different kinds of structures (the core diameter, the relative index difference, the hole position, the number of holes, and the like). This estimation method may also be applied to a holey optical fiber having the same structure. As for the holey optical fiber having different kinds of structure, the constants $a_1$, $a_2$, $b_1$, and $b_2$ may be determined respectively, and the constants may used for the estimation.

Next, a method of obtaining the hole position of the holey optical fiber, and the surface roughness of the inner surfaces of holes based on the arithmetical mean value I(x) of the holey optical fiber obtained by the bidirectional OTDR measurement technique will be described.

Figure 10:
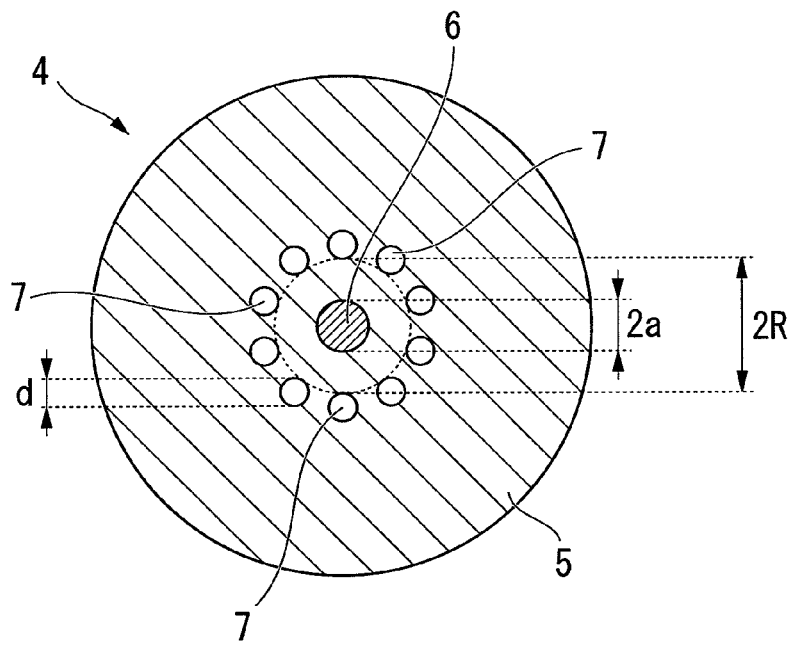
FIG. 10 is a cross-sectional view showing the hole position of a holey optical fiber.

The hole position is defined by the diameter 2R of a virtual circle that is supposed to be inscribed to the outer peripheries of all the holes 7 of the holey optical fiber, as shown in FIG. 10, and shows the distance between the center of the core 6 and the circumference of holes 7.

It is known that this hole position affects various optical properties. If the hole position is close to the core 6, due to the reduction of the confinement loss, the bending loss is reduced, and the mode field diameter becomes smaller. Moreover, this hole position also affects chromatic dispersion characteristics, and a zero dispersion wavelength or dispersion slope besides a dispersion value also varies depending on a change in the hole position. As this hole position is known, information on the bending loss, the mode field diameter, and the dispersion properties in the longitudinal direction can be obtained.

On the other hand, the surface roughness $\Gamma(x)$ of the inner surfaces of the holes 7 affects the optical loss of the holey optical fiber, and the factor of an increase in the optical loss can be identified based on information in the surface roughness.

Hereinafter, a method of obtaining the hole position and the surface roughness of the inner surfaces of holes of the holey optical fiber based on the arithmetical mean value I(x) will be described.

The arithmetical mean value I(x) of the above Formula (1) can be defined as the following Formula (7) (M. Ohashi., IEEE Photonics Tech. Lett. vol. 18, pp. 2584 to 2586, 2006).

$$I(x) = \frac{S(x) + S(L-x)}{2} = a_0 + 10\log[\alpha_s(x)B(x)] - 2(10\log e)\int_0^x \gamma(l)dl \quad (7)$$

Here, $a_0$ is a constant that does not depend on x, $\alpha_s(x)$, B(x), and $\gamma(x)$ are the local scattering coefficient, the backscattered capture ratio, and the local attenuation coefficient.

Moreover, B(x) is expressed by Formula (8), $\lambda$ is wavelength, n(x), and $2\omega(x)$ are the refractive index of the core and a mode field diameter (MFD) at x.

$$B(x) = \frac{3}{2}\left(\frac{\lambda}{2\pi n(x)\omega(x)}\right)^2 \quad (8)$$

Now, as shown in FIG. 10, a holey optical fiber that has the diameter 2a of the core 6, the relative index difference $\Delta$, the diameter d of the hole 7, and the radius R of a virtual circle inscribed to all the holes 7 will be considered. Here, the radius R of the virtual circle indicates the distance from the core 6, and can be considered to indicate the position of the holes 7 within the cladding 5, therefore the radius R or the diameter 2R denote the hole position.

The mode field diameter MFD of such a holey optical fiber is affected by the changes in 2a and $\Delta$ as well as affected by the changes in d and R (K. Nakajima et al., 58th IWCS, 9-3, 2009), and is expressed by Formula (9).

$$2\omega(x)=2\omega(a(x),\Delta(x),R(x),d(x)) \quad (9)$$

Moreover, it can be considered that the parameter $\Gamma(x)$ of the surface roughness of the holes is also a parameter that influences the backscattering light of the holey optical fiber, and the arithmetical mean value I(x) is defined in the following Formula (10).

$$I(x) = a_0 + 10\log[\alpha_s(x)B(x)\Gamma(x)] - 2(10\log e)\int_0^x \gamma(l)dl \quad (10)$$

Here, it is found that $\Delta I(x)$ obtained by normalized I(x) with $I(x_0)$ in $x=x_0$ can be expressed like Formula (8) to Formula (10), and Formula (11).

$$\Delta I(x) \equiv I(x) - I(x_0) \quad (11)$$
$$= 10\log\left[\frac{\alpha_s(x)n^2(x_0)}{\alpha_s(x_0)n^2(x)}\right] + 20\log\left[\frac{\omega(a(x_0), \Delta(x_0), R(x_0), d(x_0))}{\omega(a(x), \Delta(x), R(x), d(x))}\right] +$$
$$10\log\left[\frac{\Gamma(x)}{\Gamma(x_0)}\right]$$

Figure 11:
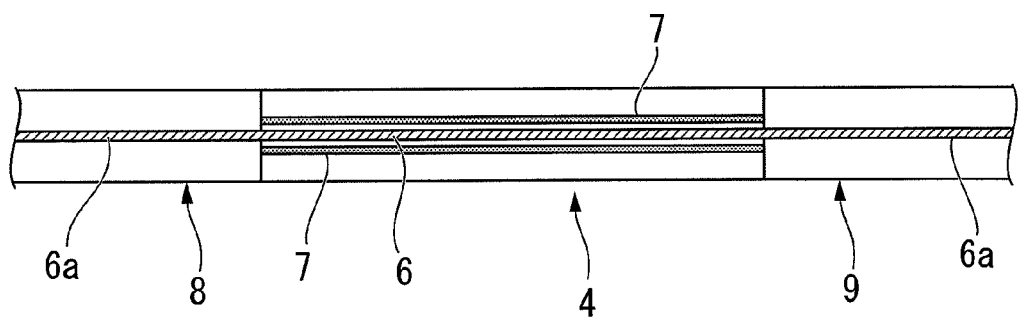
FIG. 11 is a view showing a configuration in which optical fibers for reference are connected to both ends of a holey optical fiber.

In order to prove this Formula (11), optical fibers for reference, such as single mode optical fibers that have the same core structure as the holey optical fiber that is an object to be measured, and are not formed with holes are used as the optical fibers to be referred to at $x=x_0$, these optical fibers for reference 8 and 9 are connected to both ends of the holey optical fiber 4 as shown in FIG. 11, and the bidirectional OTDR measurement is performed.

As such, when the optical fibers for reference that have the same core structure as the holey optical fiber that is an object to be measured, and are not formed with holes are used as the optical fibers to be referred to at $x=x_0$, the normalized $\Delta I(x)$ that is obtained from the bidirectional OTDR measurement can omit the core radius a(x), the relative index difference $\Delta(x)$, and the refractive index n(x) of the core at the position x from Formula (11), and be simplified into Formula (12).

$$\Delta I(x) \cong 20\log\left[\frac{\omega(R(x_0), d(x_0))}{\omega(R(x), d(x))}\right] + 10\log\left[\frac{\Gamma(x)}{\Gamma(x_0)}\right] \quad (12)$$

As the holey optical fiber used for the measurement, a plurality of samples in which the diameter d of the hole 7 is intentionally changed, and two kinds of samples in which the surface roughness of the inner surfaces of holes differs are prepared.

Figure 12:
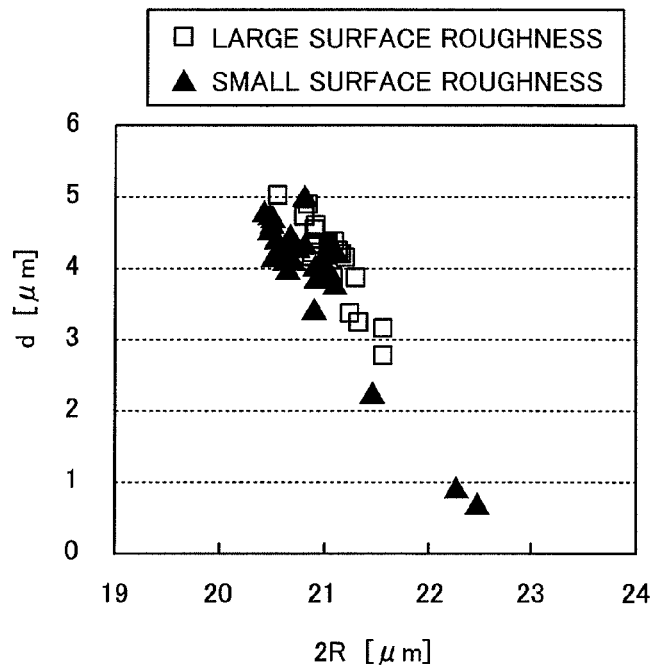
FIG. 12 is a graph showing the correlation between the internal hole diameter d, and a hole position 2R.

FIG. 12 shows the relation between the diameter d of the holes 7 and the diameter 2R of the virtual circle in the holey optical fibers of these samples. This graph shows that the diameter d and the diameter 2R have a good correlation. Additionally, it is apparent that, even if the surface roughness differs, the diameter d and the diameter 2R have a good correlation. In addition, the measurement wavelength in the bidirectional OTDR measurement is 1550 nm.

Figure 13:
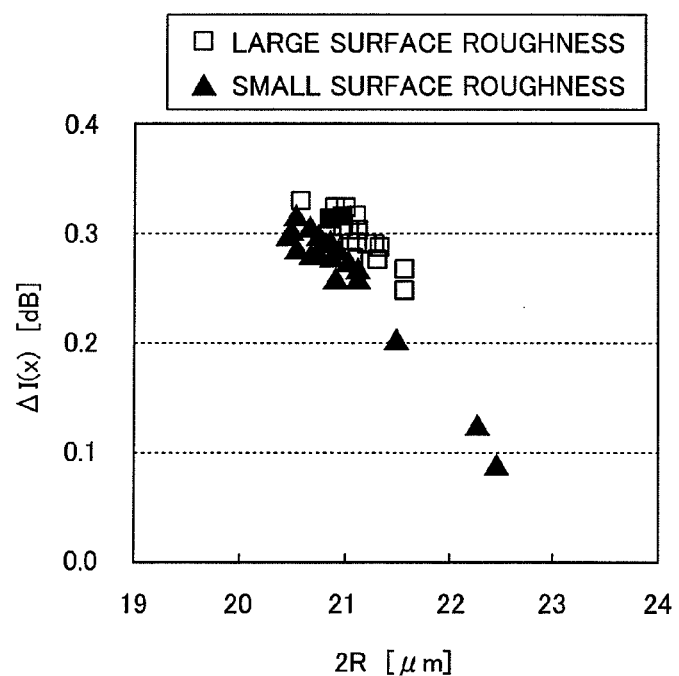
FIG. 13 is a graph showing the correlation with the difference ΔI and the hole position 2R.

FIG. 13 is a graph showing the relation between the diameter 2R of the virtual circle of the holey optical fiber measured and $\Delta I(x)$ obtained from the bidirectional OTDR measurement, as for the holey optical fibers that are the samples in which the surface roughness differs.

It is recognized that there is a strong correlation between the diameter 2R and $\Delta I(x)$ from this graph, and it turns out that this correlation is established even if the surface roughness differs. Accordingly, it can be understood that the hole position at the position (x) of the holey optical fiber, and the surface roughness of the inner surfaces of holes can be obtained based on the correlation shown in FIG. 13 by obtaining the arithmetical mean value $\Delta I(x)$ from the bidirectional OTDR measurement.

In the above description, description has been made in the form in which the bidirectional OTDR measurement is performed on a connected optical fiber obtained by connecting the optical fibers for reference 8 and 9 to both ends of the holey optical fiber 4 serving as an object to be measured. However, the invention is not limited thereto. Similarly to the previous measurement of the hole diameter and the bending loss, the hole position and the surface roughness of the inner surfaces of holes can similarly be obtained even if the optical fibers for reference are not connected.

In this case, the same analysis is possible for $\alpha_s(x_0)$, $n(x_0)$, a $(x_0)$, $\Delta(x_0)$, $R(x_0)$, $d(x_0)$, $\Gamma(x_0)$, and $I(x_0)$ in Formula (11) by adopting values at terminal points of the holey optical fiber.

In addition, the method of obtaining the arithmetical mean value by the bidirectional OTDR measuring method and estimating the hole diameter or bending loss from the arithmetical mean value has been described in the above embodiment. However, the arithmetical mean value can be obtained by the total reflection OTDR measuring method to estimate the hole diameter or the bending loss.

The specific method of calculating arithmetical mean value by the total reflection OTDR measuring method will be described in detail in the following test method of an optical line.

Next, a test method of an optical line in which the holey optical fiber of an embodiment of the invention is installed will be described.

This test method of an optical line uses the total reflection OTDR measurement technique.

Since one measurement terminal (first measurement terminal) is a terminal at a far end in the case of an installed optical line, measurement by the bidirectional OTDR method is difficult. Therefore, the total reflection OTDR measuring method is used.

Figure 14:
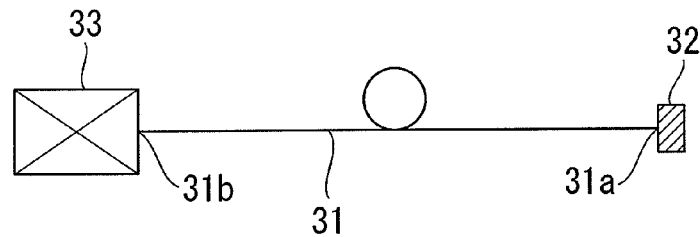
FIG. 14 is a schematic configuration view showing an embodiment of a test method of an optical line of the invention.

As shown in FIG. 14, a total reflection terminator 32 having high reflectivity is connected to a far end (first end) 31a of an installed optical fiber transmission line 31 in which the holey optical fiber is installed, and an OTDR measuring equipment 33 is connected to a near end (second end) 31b of the transmission line 31. The measurement light is made to enter the transmission line 31 from the near end 31b toward the far end 31a from the OTDR measuring equipment 33.

The optical fiber transmission line 31 may be composed of only the holey optical fibers, or may be one to which optical fibers other than the holey optical fibers are connected.

Backscattering light originating from measurement light incident from the near end 31b is received by the OTRD measuring equipment 33. The measurement light is reflected by the total reflection terminator 32, and this reflected light propagates toward the near end 31b side as measurement light that is virtually incident from the far end 31a side. Backscattering light originating from this virtual measurement light is again reflected by the total reflection terminator 32, and is received by the OTDR measuring equipment 33.

Accordingly, the backscattering light originating from the measurement light incident from the near end 31b and the backscattering light originating from the measurement light to be considered as virtually incident from the far end 31a are received in the OTDR measuring equipment 33. As a result, two backscattering light waveforms can be obtained similarly to the original bidirectional OTDR measuring method.

For example, when an optical line with a line length L is measured, backscattering light intensity at a position with a length x from the near end side (second end side) can be defined as $S_A(x)$, and backscattering light intensity at a position with a length L−x from the far end side (first end side) can be defined as $S_B(2L-x)$, and the arithmetical mean value I(x) can be obtained.

If the arithmetical mean value I(x) is obtained in this way, the hole diameter or the bending loss value can be estimated as in the above description even in an installed optical line. For example, an optical line test method that can detect a defect portion where an excessive external force is applied during the installation of an optical line or the like and the bending loss is increased becomes possible.

Additionally, as shown in FIG. 2, since the holey optical fiber shows a arithmetical mean value I(x) differs from a general-purpose single mode optical fiber, the kind of an optical fiber in an installed optical line can be identified by the present test method. For example, in a mixed line in which a single mode optical fiber and a holey optical fiber are connected in series, the kind of the optical fibers can be identified.

Moreover, as mentioned above, the hole position and the surface roughness can also be obtained based on the arithmetical mean value I(x) of the optical fiber transmission line 31.

The manufacturing method of a holey optical fiber of an embodiment of the invention has a series of processes of melting and drawing an holey optical fiber preform as a holey optical fiber, and estimating the hole diameter, bending loss, hole position, and the surface roughness of the inner surfaces of holes in the holey optical fiber, using the aforementioned measuring method.

In such a manufacturing method, there is an advantage that the hole diameter, bending loss, hole position, and surface roughness of the produced holey optical fiber can be obtained, and the optical fiber can be shipped as a product that guarantees characteristic values, such as a bending loss value. Additionally, a holey optical fiber that keeps characteristic values, such as the bending loss value, within prescribed values can be manufactured.

Figure 15:
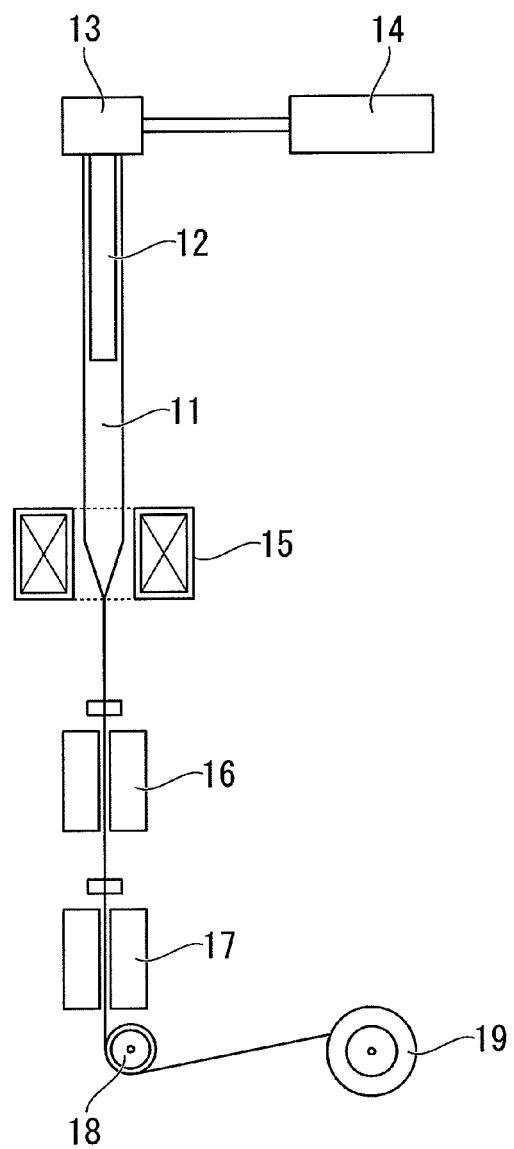
FIG. 15 is a schematic configuration view showing an embodiment of a manufacturing method of the invention.

FIG. 15 shows one embodiment of the manufacturing method of the invention, and shows the portion of a first process.

In FIG. 15, reference numeral 11 designates a holey optical fiber preform. The holey optical fiber preform 11 is obtained, for example, by a method of performing drilling work on a hole-less optical fiber preform. A base end portion of the holey optical fiber preform 11 is gripped by a grip part (not shown) so as to be rotatable and movable up and down. Additionally, a gas introduction pipe 12 is airtightly connected to the base end portion of the holey optical fiber preform 11, and pressurized gas, such as dry nitrogen gas, is sent into the holes of the holey optical fiber preform 11 as will be described below such that the space within the holes has a predetermined pressure.

The gas introduction pipe 12 is connected to a pressurized gas supply source 14 via a relay box 13, and the pressurized gas whose pressure is adjusted is sent into the holes of the holey optical fiber preform 11 through the relay box 13 and the gas introduction pipe 12 from the pressurized gas supply source 14. Thereby, a predetermined diameter can be held without collapse of the holes during melting and drawing of the holey optical fiber preform 11, and a holey optical fiber wire with a predetermined hole diameter can be obtained.

A distal end side of the holey optical fiber preform 11 is arranged within a melting furnace 15, and is melted and drawn from its distal end portion, whereby a bare holey optical fiber wire is obtained. The bare holey optical fiber wire is subsequently guided to a first coating apparatus 16 and a second coating apparatus 17, and a primary coating layer and a secondary coating layer are provided and are made into a holey optical fiber wire. This holey optical fiber wire is taken over by a taking-over apparatus 18, and is wound around a bobbin 19. The above process becomes the first process of the manufacturing method of an embodiment of the invention.

Subsequently, it is necessary to know characteristic values, such as the bending loss value, for the purpose of quality guarantee of the holey optical fiber wire produced in the first process. For this reason, in the manufacturing method of the embodiment of the invention, quality can be guaranteed by estimating the hole diameter, the bending loss value, the hole position, and the hole surface roughness according to the aforementioned measuring method. Measurement of the hole diameter, the bending loss value, the hole position, and the hole surface roughness is a second process of the manufacturing method of the embodiment of the invention.

As such, in the manufacturing method of the embodiment of the invention, it is possible to guarantee characteristics, such as the bending loss value of the manufactured holey optical fiber, and a user can be provided with a highly reliable and stable holey optical fiber. Additionally, a holey optical fiber that keeps characteristic values, such as the bending loss value, within prescribed values can be manufactured.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A manufacturing method of a holey optical fiber, comprising:
    manufacturing a holey optical fiber by melting and drawing an optical fiber preform formed with holes; and
    measuring a hole diameter of the holey optical fiber by using a hole diameter-measuring method,
    the hole diameter-measuring method comprising:
    preparing first holey optical fibers with different first hole diameters;
    obtaining first arithmetical mean values as a result of calculating a first arithmetical mean value $I(x_{p1})$ from two backscattering light intensities at a position $x_{p1}$ of two backscattering light waveforms of each of the first holey optical fibers, in which the two backscattering light waveforms are obtained by OTDR measurement;
    obtaining first mode field diameters, each of which is defined by a first mode field diameter $2W(x_{p1})$ which is calculated by using the first arithmetical mean value $I(x_{p1})$ and formula (3) or formula (4);

$$2W(x)=2W(x_0)\cdot 10^{((-(I(x)-I(x0))+k)/20)} \quad (3)$$

$2W(x_0)$: a mode field diameter at a position $x_0$ of an optical fiber for reference or a first terminal point of each of the holey optical fibers;
$I(x_0)$: an arithmetical mean value at the position $x_0$ of the optical fiber for reference or the first terminal point of each of the holey optical fibers;
k: a constant expressed by the following formula;

$$k = 10\cdot \log\left[\left\{\frac{1+0.62\Delta(x)}{1+0.62\Delta(x_0)}\right\}\left\{\frac{50-\Delta(x)}{50-\Delta(x_0)}\right\}\right]$$

$$2W(x)=2W(x_0)\cdot [2W(x_1)/2W(x_0)]^{((I(x)-I(x0))/(I(x1)-I(x0)))} \quad (4)$$

$2W(x_0)$: a mode field diameter at the position $x_0$ of the optical fiber for reference or the first terminal point of each of the holey optical fibers;
$2W(x_1)$: a mode field diameter at a position $x_1$ of the optical fiber for reference or a second terminal point of each of the holey optical fibers;
$I(x_0)$: an arithmetical mean value at the position $x_0$ of the optical fiber for reference or the first terminal point of each of the holey optical fibers;
$I(x_1)$: an arithmetical mean value at the position $x_1$ of the optical fiber for reference or the second terminal point of each of the holey optical fibers;
obtaining the first hole diameters of the first holey optical fibers, the first hole diameters being actually measured using an offline measurement method;
drawing a graph by obtaining datapoints, each of which is defined by each of the obtained first mode field diameters and each of the obtained first hole diameters;
acquiring a relational expression (5) between the obtained first mode field diameters and the obtained first hole diameters as a result s of approximating the datapoints by a linear function;

$$d \approx a_1+a_2\times 2W \quad (5)$$

d: a hole diameter;
$a_1$: a first constant value obtained by approximating the datapoints by the linear function;
$a_2$: a second constant value obtained by approximating the datapoints by the linear function;
preparing a second holey optical fiber which is different from the first holey optical fibers;
calculating a second arithmetical mean value $I(x_{p2})$ from two backscattering light intensities at a position $x_{p2}$ of two backscattering light waveforms of the second holey optical fiber, in which the two backscattering light waveforms are obtained by OTDR measurement;
obtaining a second mode field diameter $2W(x_{p2})$ using the second arithmetical mean value $I(x_{p2})$ and formula (3) or formula (4); and
obtaining a second hole diameter at the position $x_{p2}$, based on the second mode field diameter $2W(x_{p2})$ and the relational expression (5).

2. A manufacturing method of a holey optical fiber, comprising:
    manufacturing a holey optical fiber by melting and drawing an optical fiber preform formed with holes; and
    measuring a bending loss of the holey optical fiber by using a bending loss-measuring method,
    the bending loss-measuring method comprising:
    preparing first holey optical fibers with different first bending losses and different first hole diameters;
    obtaining the first bending losses of the first holey optical fibers, the first bending losses being actually measured using an offline measurement method;
    drawing a graph by obtaining datapoints, each of which is defined by each of the first hole diameters obtained by the measuring method according to claim 1 and each of the obtained first bending losses;
    acquiring a relational expression (6) between the obtained first hole diameters and the obtained first bending losses as a result of approximating the datapoints by an exponential function;

$$\alpha_b \approx b_1 \times \exp(b_2 \times d) \quad (6)$$

d: diameter obtained by the measuring method according to claim 1;

$b_1$: a first constant value obtained by approximating the datapoints by the exponential function;

$b_2$: a second constant value obtained by approximating the datapoints by the exponential function;

preparing a second holey optical fiber which is different from the first holey optical fibers; and obtaining a second bending loss at the position $x_{p2}$, based on the relational expression (6) and a second hole diameter of the second holey optical fiber obtained by the measuring method according to claim 1.

3. The measuring method of a bending loss of a holey optical fiber according to claim 2, further comprising:

deriving a mode field diameter $2W(x)$ using the arithmetical mean value $I(x)$; and obtaining the bending loss value at the position x, based on a correlation between a mode field diameter $2W(x)$ and a bending loss value of the holey optical fiber that is obtained in advance.

4. The measuring method of a hole diameter of a holey optical fiber according to claim 1, further comprising:

calculating an arithmetical mean value $I_{ref}$ at an optical fiber portion for reference to both ends of the holey optical fiber;

obtaining a difference $\Delta I$ between the arithmetical mean value $I(x)$ and the arithmetical mean value $I_{ref}$; and obtaining the hole diameter at the position x, based on a correlation between a difference $\Delta I$ and a hole diameter of the holey optical fiber that is obtained in advance.

5. The measuring method of a hole diameter of a holey optical fiber according to claim 4, wherein the optical fiber for reference is a single mode optical fiber.

6. The measuring method of a hole position of a holey optical fiber according to claim 1, further comprising:

calculating an arithmetical mean value $I_{ref}$ at an optical fiber portion for reference;

obtaining a difference $\Delta I$ between the arithmetical mean value $I(x)$ and the arithmetical mean value $I_{ref}$; and obtaining the hole position at the position x, based on a correlation between a difference $\Delta I$ and a hole position of the holey optical fiber that is obtained in advance, wherein the two backscattering light waveforms are obtained from a connected optical fiber formed by connecting optical fibers for reference to both ends of the holey optical fiber respectively.

7. The measuring method of a hole position of a holey optical fiber according to claim 6, wherein the optical fiber for reference is a single mode optical fiber.

8. The measuring method of a hole diameter of a holey optical fiber according to claim 1, further comprising:

deriving a mode field diameter $2W(x)$ using the arithmetical mean value $I(x)$; and obtaining the hole diameter at the position x, based on a correlation between a mode field diameter $2W(x)$ and a hole diameter of the holey optical fiber that is obtained in advance.

9. A manufacturing method of a holey optical fiber, comprising:

manufacturing a holey optical fiber by melting and drawing an optical fiber preform formed with holes; and measuring a hole position of the holey optical fiber by using a hole position-measuring method, the hole position-measuring method comprising:

preparing a second holey optical fiber;

calculating an arithmetical mean value $I(x)$ from two backscattering light intensities at a position x of two backscattering light waveforms of the holey optical fiber, in which the two backscattering light waveforms are obtained by OTDR measurement;

obtaining a mode field diameter $2W(x)$ using the arithmetical mean value $I(x)$ and formula (3) or formula (4);

$$2W(x)=2W(x_0)\cdot 10^{((-I(x)\cdot I(x0))+k)/20)} \quad (3)$$

$2W(x_0)$: a mode field diameter at a position $x_0$ of an optical fiber for reference or a first terminal point of each of the holey optical fibers;

$I(x_0)$: an arithmetical mean value at the position $x_0$ of the optical fiber for reference or the first terminal point of each of the holey optical fibers;

k: a constant expressed by the following formula;

$$k = 10 \cdot \log\left[\left\{\frac{1+0.62\Delta(x)}{1+0.62\Delta(x_0)}\right\}\left\{\frac{50-\Delta(x)}{50-\Delta(x_0)}\right\}\right]$$

$$2W(x)=2W(x_0)\cdot [2W(x_1)/2W(x_0)]^{((I(x)\cdot I(x0))/(I(x1)\cdot I(x0)))} \quad (4)$$

$2W(x_0)$: a mode field diameter at the position $x_0$ of the optical fiber for reference or the first terminal point of each of the holey optical fibers;

$2W(x_1)$: a mode field diameter at a position $x_1$ of the optical fiber for reference or a second terminal point of each of the holey optical fibers;

$I(x_0)$: an arithmetical mean value at the position $x_0$ of the optical fiber for reference or the first terminal point of each of the holey optical fibers;

$I(x_1)$: an arithmetical mean value at the position $x_1$ of the optical fiber for reference or the second terminal point of each of the holey optical fibers; and obtaining a hole position $2R(x)$ at the position x, based on the relational expression (12) and the obtained mode field diameter $2W(x)$:

$$\Delta I(x) \cong 20\log\left[\frac{\omega(R(x_0), d(x_0))}{\omega(R(x), d(x))}\right] + 10\log\left[\frac{\Gamma(x)}{\Gamma(x_0)}\right] \quad (12)$$

$R(x_0)$: a radius of a virtual circle that is supposed to be inscribed to an outer peripheries of all holes of the holey optical fiber at the position $x_0$;

$d(x_0)$: an internal hole diameter at the position $x_0$;

$d(x)$: an internal hole diameter at the position x;

$\Gamma(x_0)$: a hole surface roughness of the holey optical fiber at the position $x_0$;

$\Gamma(x)$: a hole surface roughness of the holey optical fiber at the position x;

$\omega(R(x_0), d(x_0))$: a mode field radius of the holey optical fiber at the position $x_0$;

$\omega(R(x), d(x))$: a mode field radius of the holey optical fiber at the position x.

10. The measuring method of a bending loss of a holey optical fiber according to claim 9, further comprising:

calculating an arithmetical mean value $I_{ref}$ at an optical fiber portion for reference;

obtaining a difference $\Delta I$ between the arithmetical mean value $I(x)$ and the arithmetical mean value $I_{ref}$; and obtaining the bending loss at the position x, based on a correlation between a difference $\Delta I$ and a bending loss of the holey optical fiber that is obtained in advance, wherein the two backscattering light waveforms are obtained from a connected optical fiber formed by connecting optical fibers for reference to both ends of the holey optical fiber respectively.

11. The measuring method of the bending loss of a holey optical fiber according to claim 10,
wherein the optical fiber for reference is a single mode optical fiber.

12. The measuring method of a hole surface roughness of a holey optical fiber according to claim 9, further comprising:
calculating an arithmetical mean value $I_{ref}$ at an optical fiber portion for reference;
obtaining a difference $\Delta I$ between the arithmetical mean value $I(x)$ and the arithmetical mean value $I_{ref}$; and
obtaining the surface roughness of the holes at the position x, based on a correlation between a difference $\Delta I$ and a surface roughness of the holes of the holey optical fiber that is obtained in advance,
wherein the two backscattering light waveforms are obtained from a connected optical fiber formed by connecting optical fibers for reference to both ends of the holey optical fiber respectively.

13. The measuring method of a hole surface roughness of a holey optical fiber according to claim 12,
wherein the optical fiber for reference is a single mode optical fiber.

14. A manufacturing method of a holey optical fiber, comprising:
manufacturing a holey optical fiber by melting and drawing an optical fiber preform with holes; and
measuring a hole surface roughness of the holey optical fiber by using a hole surface roughness-measuring method,
the hole surface roughness-measuring method comprising:
preparing a holey optical fiber;
calculating an arithmetical mean value $I(x)$ from two backscattering light intensities at a position x of two backscattering light waveforms of the holey optical fiber, in which the two backscattering light waveforms are obtained by OTDR measurement;
obtaining a mode field diameter $2W(x)$ using the arithmetical mean value $I(x)$ and formula (3) or formula (4):

$$2W(X) = 2W(x_0) \cdot 10^{(-(I(x)-I(x0))+k)/20)} \quad (3)$$

$2W(x_0)$: a mode field diameter at a position $x_0$ of an optical fiber for reference or a first terminal point of each of the holey optical fibers;
$I(x_0)$: an arithmetical mean value at the position $x_0$ of the optical fiber for reference or the first terminal point of each of the holey optical fibers;
k: a constant expressed by the following formula;

$$k = 10 \cdot \log\left[\left\{\frac{1+0.62\Delta(x)}{1+0.62\Delta(x_0)}\right\}\left\{\frac{50-\Delta(x)}{50-\Delta(x_0)}\right\}\right]$$

$$2W(x) = 2W(x_0) \cdot [2W(x_1)/2W(x_0)]^{((I(x)-I(x0))/(I(x1)-I(x0)))} \quad (4)$$

$2W(x_0)$: a mode field diameter at the position $x_0$ of the optical fiber for reference or the first terminal point of each of the holey optical fibers;
$2W(x_1)$: a mode field diameter at a position $x_1$ of the optical fiber for reference or a second terminal point of each of the holey optical fibers;
$I(x_0)$: an arithmetical mean value at the position $x_0$ of the optical fiber for reference or the first terminal point of each of the holey optical fibers;
$I(x_1)$: an arithmetical mean value at the position $x_1$ of the optical fiber for reference or the second terminal point of each of the holey optical fibers; and
obtaining a surface roughness $\Gamma(x)$ of the holes at the position x, based on the relational expression (12) and the obtained mode field diameter $2W(x)$:

$$\Delta I(x) \cong 20\log\left[\frac{\omega(R(x_0), d(x_0))}{\omega(R(x), d(x))}\right] + 10\log\left[\frac{\Gamma(x)}{\Gamma(x_0)}\right] \quad (12)$$

$R(x_0)$: a radius of a virtual circle that is supposed to be inscribed to an outer peripheries of all holes of the holey optical fiber at the position $x_0$;
$R(x)$: a radius of a virtual circle that is supposed to be inscribed to an outer peripheries of the all holes of the holey optical fiber at the position x;
$d(x_0)$: an internal hole diameter at the position $x_0$;
$d(x)$: an internal hole diameter at the position x;
$\Gamma(x_0)$: a hole surface roughness of the holey optical fiber at the position $x_0$;
$\omega(R(x_0), d(x_0))$: a mode field radius of the holey optical fiber at the position $x_0$;
$\omega(R(x), d(x))$: a mode field radius of the holey optical fiber at the position x.

15. A manufacturing method of a holey optical fiber, comprising:
manufacturing a holey optical fiber by melting and drawing an optical fiber preform formed with holes; and
measuring a hole diameter of the holey optical fiber by using a hole diameter-measuring method,
the hole diameter-measuring method comprising:
preparing first holey optical fibers with different first hole diameters;
obtaining first arithmetical mean values as a result of calculating a first arithmetical mean value $I(x_1)$ from two backscattering light intensities at a position $x_1$ of two backscattering light waveforms of each of the first holey optical fibers, in which the two backscattering light waveforms are obtained by OTDR measurement;
obtaining the first hole diameters of the first holey optical fibers, the first hole diameters being actually measured using an offline measurement method;
drawing a graph by obtaining datapoints, each of which is defined by each of the first arithmetical mean values and each of the obtained first hole diameters;
acquiring a relational expression (1) between the obtained first arithmetical mean values and the obtained first hole diameters as a results of approximating the datapoints by a linear function;

$$d = A + B \times I(x) \quad (1)$$

d: a hole diameter;
A: a first constant value obtained by approximating the datapoints by the linear function;
B: a second constant value obtained by approximating the datapoints by the linear function;
preparing a second holey optical fiber which is different from the first holey optical fibers;
calculating a second arithmetical mean value $I(x_2)$ from two backscattering light intensities at a position $x_2$ of two backscattering light waveforms of the second holey optical fiber, in which the two backscattering light waveforms are obtained by OTDR measurement,
calculating a second arithmetical mean value $I(x_2)$ from two backscattering light intensities at a position $x_2$ of two backscattering light waveforms of the second holey optical fiber, in which the two backscattering light waveforms are obtained by OTDR measurement; and obtaining a second hole diameter at the position $x_2$, based on the calculated second arithmetical mean value $I(x_2)$ and the relational expression (1).

16. A manufacturing method of a holey optical fiber, comprising:

manufacturing a holey optical fiber by melting and drawing an optical fiber preform formed with holes; and measuring a bending loss of the holey optical fiber by using a bending loss-measuring method, the bending loss-measuring method comprising:

preparing first holey optical fibers with different first bending losses;

obtaining first arithmetical mean values as a result of calculating a first arithmetical mean value $I(x_1)$ from two backscattering light intensities at a position $x_1$ of two backscattering light waveforms of each of the first holey optical fibers, in which the two backscattering light waveforms are obtained by OTDR measurement;

obtaining the first bending losses of the first holey optical fibers, the first bending losses being actually measured using an offline measurement method;

drawing a graph by obtaining datapoints, each of which is defined by each of the calculated first arithmetical mean values and each of the obtained first bending losses;

acquiring a relational expression (1) between the first arithmetical mean values and the obtained first bending losses as a result of approximating the datapoints by an exponential function;

$$\alpha_b = A \times \exp(B \times I(x)) \qquad (1)$$

$\alpha_b$: a bending loss;

A: a first constant value obtained by approximating the datapoints by the exponential function;

B: a second constant value obtained by approximating the datapoints by the exponential function;

preparing a second holey optical fiber which is different from the first holey optical fibers;

calculating a second arithmetical mean value $I(x_2)$ from two backscattering light intensities at a position $x_2$ of two backscattering light waveforms of the second holey optical fiber, in which the two backscattering light waveforms are obtained by OTDR measurement; and obtaining a second bending loss at the position $x_2$, based on the calculated second arithmetical mean value $I(x_2)$ and the relational expression (1).

* * * * *